United States Patent
Klimko

(12) 
(10) Patent No.: US 6,300,328 B1
(45) Date of Patent: Oct. 9, 2001

(54) SELECTIVE INHIBITORS OF ADENOSINE MONOPHOSPHATE DEAMINASE FOR THE TREATMENT OF OPTIC NERVE AND RETINAL DAMAGE

(75) Inventor: Peter G. Klimko, Fort Worth, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/627,914

(22) Filed: Jul. 28, 2000

Related U.S. Application Data

(60) Provisional application No. 60/147,605, filed on Aug. 6, 1999.

(51) Int. Cl.$^7$ ..................................................... A61K 31/55
(52) U.S. Cl. ........................... 514/221; 514/912; 514/913
(58) Field of Search ................................... 514/221, 912, 514/913

(56) References Cited

U.S. PATENT DOCUMENTS

| | | | |
|---|---|---|---|
| 4,550,022 | 10/1985 | Garabedian et al. | 424/127 |
| 4,912,092 | 3/1990 | Gruber | 514/45 |
| 5,049,586 | 9/1991 | Ortega et al. | 514/557 |
| 5,731,432 | 3/1998 | Erion et al. | 540/568 |
| 5,780,450 | 7/1998 | Shade | 514/46 |

OTHER PUBLICATIONS

Erion, et al., "Discovery of AMP Mimetics that Exhibit High Inhibitory Potency and Specificity for AMP Deaminase," *J. Am. Chem. Soc.*, vol. 121:308–319, 1999.

Erion, M.D., "Chapter 31. Adenosine Receptors as Pharmacological Targets," *Annual Reports in Medicinal Chemistry*; vol. 288:295–304, 1993.

DeNinno, M.P. "Chapter 11. Adenosine," *Annual Reports in Medicinal Chemistry*, vol. 33:111–120.

Ghiardi, et al., "The purine nucleoside adenosine in retinal ischemia–reperfusion injury," *Vision Research*, vol. 39:2519–2535, 1999.

*Primary Examiner*—Zohreh Fay
(74) *Attorney, Agent, or Firm*—Sally S. Yeager

(57) ABSTRACT

Selective AMPDA inhibitors for preventing and treating damage to the optic nerve and/or retina are disclosed.

2 Claims, No Drawings

SELECTIVE INHIBITORS OF ADENOSINE MONOPHOSPHATE DEAMINASE FOR THE TREATMENT OF OPTIC NERVE AND RETINAL DAMAGE

This application claims priority from U.S. Provisional Application Ser. No. 60/147,605, filed Aug. 6, 1999.

This invention concerns compounds which inhibit the enzyme adenosine monophosphate deaminase (AMPDA) for the treatment of optic nerve and retinal damage resulting from ischaemia and hypoxia.

BACKGROUND OF THE INVENTION

The cytoprotective effects resulting from adenosine receptor activation, such as, vasodilation, neurotransmission inhibition, reduced oxygen consumption, and reduced inflammation are well known in the art (see for example: Erion, M. D., Ann. Rep. Med. Chem. 1993, 288, 295; DeNinno, M. P., Ann. Rep. Med. Chem. 1998, 33, 111). Several compounds which are either agonists at one of the adenosine receptor sub-types or which maintain/increase adenosine levels in affected tissue by preventing adenosine catabolism have been evaluated in animals and man for the treatment of damage resulting from stroke, brain trauma, and heart attack. One method of increasing adenosine concentration in the affected tissue is to inhibit the AMPDA-catalyzed deamination of adenosine monophosphate (AMP), an intermediate in the biochemical pathway between adenosine triphosphate and adenosine, to inosine monophosphate. However, such inhibition needs to be selective for AMPDA over adenosine deaminase (ADA), as potent ADA inhibition has been observed to result in severe immunosuppresion.

Compounds which inhibit the uptake of adenosine have been claimed for the treatment of retinal and optic neuropathy (Shade, U.S. Pat. No. 5,780,450), and a method for preventing retinal damage by administering a purine nucleoside analog has been claimed (Gruber, U.S. Pat. No. 4,912,092). The effect of elevated adenosine concentration on tissue damage in animal models of retinal ischaemia-reperfusion injury has been reviewed (Ghiardi, G. J.; Gidday, J. M.; Roth, S. Vision Research 1999, 39, 2519). Also, the compounds of the present invention have been claimed for the treatment of heart and nerve tissue damage resulting from ischaemic events (Erion, U.S. Pat. No. 5,731,432; Erion et. al., J. Am Chem. Soc. 1999, 121, 308). However, the compounds of the present invention have not been claimed or disclosed for the treatment of retinal and optic nerve damage resulting from ischaemia or hypoxia.

SUMMARY OF THE INVENTION

The present invention is directed to certain compounds which selectively inhibit AMPDA over the enzyme ADA for use in treating persons suffering from chronic or acute optic nerve and/or retinal damage resulting from hypoxia or ischaemia related to glaucoma, edema, or trauma. The present invention discloses compositions and methods for systemic, topical, and intraocular administration of at least one AMPDA inhibitor in an amount effective to prevent or to treat retinal and/or optic nerve head tissue damage.

DETAILED DESCRIPTION PREFERRED EMBODIMENTS

In accordance with the present invention and as used herein, the following terms are defined with the following meanings, unless explicitly stated otherwise.

The term "aryl" refers aromatic groups which have at least one ring having a conjugated pi electron system and includes carbocyclic aryl, heterocyclic aryl and biaryl groups, all of which may be optionally substituted. Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

The term "biaryl" represents aryl groups containing more than one aromatic ring including both fused ring systems and aryl groups substituted with other aryl groups.

The term "alicyclic" means compounds which combine the properties of aliphatic and cyclic compounds and include but are not limited to aromatic, cycloalkyl and bridged cycloalkyl compounds.

The term "optionally substituted" or "substituted" includes groups substituted by one to four substituents, independently selected from lower alkyl, lower aryl, lower aryloxy, aralkyl, perhaloakloxy, aralkoxy, heteroaryl, heteroaryloxy, heteroarylalkyl, heteroaralkoxy, azido, amino, guanidino, tetrazolo, 3H-1,2,3,5-oxythiodiazolo, thiazolidine-2,4-diono, oxazolidin-2,4-diono, halogen, hydroxy, lower alkoxy, lower alkylthio, carboxyalkyl, carboxyl, carboxamido, carboxamidoalkylaryl, carboxamidoaryl, aminocarboxainidoalkyl, cyano, and lower perhaloalkyl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such as with up to and including 10, preferably up to and including and advantageously one or two carbon atoms. Such groups may be straight chain or branched.

The terms "arylamino" (a), and "aralkylamino" (b), respectively, refer to the group —NRR$^1$ wherein respectively, (a) R is aryl and R$^1$ is hydrogen or aryl, and (b) R is aralkyl and R$^1$ is hydrogen or aralkyl.

The term "alkylamino" refers to —NRR$^1$ where R and R$^1$ are independently selected from hydrogen or lower alkyl.

The term "carboxamide" or "carboxamido" refers to —CONR$_2$ where each R is independently hydrogen or alkyl.

The term "alkyl" refers to saturated aliphatic groups including straight chain, branched chain and cyclic groups.

The terms "alkenyl" refers to unsaturated groups which contain at least one carbon-carbon double bond and includes straight chain, branched-chain and cyclic groups.

The term "alkynyl" refers to unsaturated groups which contain at least one carbon-carbon triple bond and includes straight chain, branched-chain and cyclic groups.

The terms "alkylene" refers to a divalent straight chain or branched chain saturated aliphatic radical.

The term "acyloxy" refers to the ester group —O—C(O)R.

The term "thioacyloxy" refers to the thioester group —S—C(O)R.

The term "alkylenylaryl" refers to an alkylene group substituted with an aryl group. "Lower alkylenylaryl" refers to such groups where alkylene is lower alkylene.

The term "alkylenylamino" refers to the group —alk— wherein alk is an alkylene group.

The term "alkylenylaminoalkylene" refers to the group —alk—NH—alk— wherein each alk is an independently selected alkylene. "Lower alkylenylaminoalkylene" refers to groups where each alkylene group is lower alkylene.

The term "alkylenylaminoaryl" refers to an alkylene group substituted with an arylamino group. In "lower alkenylaminoaryl", the alkylene group is lower alkylene.

The term "alkylenyloxyaryl" refers to an alkylene group substituted with an aryloxy group. In "lower alkylenyloxyaryl", the alkylene group is lower alkylene.

The term "alkylenylacylamino" refers to the group —alk—NH—(COR)— wherein alk is alkylene and R is lower alkyl. In "lower alkylenylacylamino", the alkylene group is lower alkylene.

The term "alkylenyloxyalkylenylaryl" refers to an alkylene group substituted with an aralkenyloxy group. "Lower alkylenyloxyalkylenylaryl" refers to such groups where the alkylene group is lower alkylene.

The term "alkylenylacylaminoalkylene" refers to the group —alk—NH—(COR)—alk— where each alk is an independently selected alkylene group. In "lower alkylenylacylaminoalkylene" the alkylene groups are lower alkylene.

The term "alkenyloxy" refers to the group —alk—O— wherein each alk is an alkylene group.

The term "alkoxyalkyl" refers to the group —alk—O— alk wherein each alk is an independently selected alkylene group. In "lower alkoxyalkyl", each alkylene is lower alkylene.

The term "alkylenethio" refers to the group —alk—S— wherein alk is alkylene group.

The term "alkylthioalkyl" refers to the group —alk—S— alk wherein each alk is an independently selected alkylene group. In "lower alkylthioalkyl" each alkylene is lower alkylene.

The term "alkylcarboxamidoalkyl" refers to the group "alk—C(O)N(R)—alk— wherein each alk is an independently selected alkylene group and R is lower alkyl. In "lower alkylcarboxamidoalkyl", each alkylene is lower alkylene.

The term "alkylcarboxamidoalkylaryl" refers to the group —$alk_1$—C(O)—NH—$alk_2$(Ar)— wherein $alk_1$ and $alk_2$ are independently selected alkylene groups and $alk_2$ is substituted with an aryl group. Ar. In "lower alkylcarboxamidoalkylaryl", each alkylene is lower alkylene.

The term "heteroalicyclic" refers to an alicyclic group having 1 to 5 heteroatoms selected from nitrogen, sulfur, phosphorus and oxygen.

The term "aminocarboxamidoalkyl" refers to the group —NH—C(O)—N(R—R) wherein each R is an independently selected alkyl group. "Lower aminocarboxamidoalkyl" refers to such groups wherein each R is lower alkyl. The term "heteroarylalkyl" refers to an alkyl group substituted with a heteroaryl group.

The term "CONH-amino acid" refers to a carbonyl bound to the N-terminus of an amino acid.

The term "coformycin aglycone" refers to 3', 6', 7', 8'-tetrahydroimidazo [4', 5'-d][1', 3'] diazepin-8-ol.

The term "prodrug" as used herein refers to any compound that when administered to a biological system generates the "drug" substance either as a result of spontaneous chemical reaction(s) or by enzyme catalyzed or metabolic reaction(s). Reference is made to various prodrugs, such as alkyl, aralkyl, aryl, etc., esters, amides, carbonates, carbamates, and urethanes of carboxylic and phosphonic acids, and acylated or alkylated hydroxyl groups included herein. The groups illustrated are exemplary, not exhaustive and one skilled in the art could prepare other known varieties of prodrugs. Such prodrugs of the compounds of Formula I fall within the scope of the present invention.

The term "pharmaceutically acceptable salt" includes salts of compounds of Formula I derived from the combination of a compound of this invention and an organic or inorganic acid or base and means any cationic salt that would be suitable for therapeutic administration to a patient by any conventional means without significant deleterious health consequences. Similarly, the term "pharmaceutically acceptable ester/amide/carbamate/carbonate/urethane," means any ester/amide/carbamate/carbonate/urethane that would be suitable for therapeutic administration to a patient by any conventional means without significant deleterious health consequences. The compounds of Formula I are useful in both free base, free acid, and salt (protonated amine or carboxylate or phosphonate anion) form. In practice the use of a salt form amounts to use of the corresponding free acid or base form; all such forms are within the scope of the present invention.

The compounds which selectively inhibit AMPDA and are useful according to this invention are represented by Formula I:

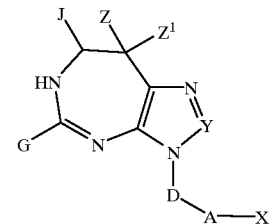

wherein:
Y=—C(K)—;
K=H, halo, azido, or amino;
G=H lower alkyl, amino;
Z=azido, hydroxy, thio, lower acyloxy, or lower thioacyloxy;
Z'=H or lower alkyl;
J=H or lower alkyl;
B=straight or branched divalent group selected from lower alkylene, lower alkylenylaryl, lower alkylenylamino, lower alkylenylaminoalkylene, lower alkylenylaminoaryl, lower alkylenyloxyaryl, lower alkylenylacylamino, lower alkylenyloxyalkylenylaryl, lower alkylenylacylaminoalkylene, lower alkyleneoxy, lower alkoxyalkyl, lower alkylenethio, lower alkylthioalkyl, lower alkynyl, lower alkenyl, alkylcarboxamidoalkyl, alkylcarboxamidoalkylaryl, hydroxylated lower alkylene, halogenated lower alkylene, halogenated lower alkylenylaryl, alkylenetetrazolo, alkylene-3H-1,2,3,5-oxythiodiazolo, alkylenethiazolidine-2,4-diono, alkyleneoxazolidin-2,4-diono or is a direct link;
A=a divalent group selected from a straight or branched alicyclic group, a straight or branched heteroalicyclic group, aryl group or heteroaryl group, all optionally substituted with substituents independently selected from lower alkyl, lower aryl, lower aryloxy, aralkyl, perhaloalkoxy, aralkoxy, heteroaryl, heteroaryloxy, heteroarylalkyl, heteroaralkoxy, azido, amino, guanidino, halogen, hydroxy, lower alkoxy, lower alkylthio, carboxyalkyl, carboxyl, carboxamido, carboxamidoalkylaryl, carboxamidoaryl, aminocarboxamidoalkyl, cyano, lower perhaloalkyl, or is a direct link;

X=H, lower alkyl, lower alkoxy, halogen, OH, acyloxy, thio, amino, azido, cyano, carboxyl carboxyalkyl, carboxyaryl, carboxyaralkyl, tetrazolo, 3H-1,2,3,5-oxythiodiazolo, thiazolidine-2,4-diono, oxazolidin-2,4-diono, carboxamido, carboxamidoalkyl, carboxamidoaralkyl, carboxamidoaryl, guanidino, -PO3EE', or C(W)CO2 E(COQ);

E and E'=same or different=H, lower alkyl, aryl or aralkyl;

W=H, lower alkyl, lower alkoxy, aralkoxy, lower alkylthio, alkylamino, OH, amino, arylamino, aralkylamino or aryloxy;

Q=lower alkyl, lower alkoxy, aralkoxy, lower alkylthio, alkylamino, OH, amino, arylamino, aralkylamino or aryloxy;

and pharmaceutically acceptable salts and prodrugs thereof.

For the purposes of nomenclature, the coformycin aglycone numbering and nucleus is shown below:

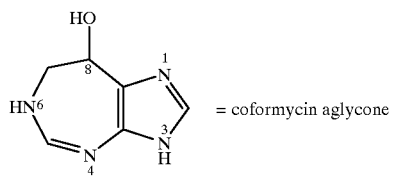 = coformycin aglycone

Especially preferred are (1'S,2'S,5'S)-3-(6',6'-dimethyl [3.1.1]-bicyclohept-2'-methyl)coformycin aglycone; 3-(5'-carboxy-6'-phenylhexyl)coformycin aglycone; 3-(5'-carbox-N-benzylamido-5'-carboxyhexyl)coformycin aglycone; 3-(2'-(3"-carboxy-6"-methylphenyl)ethyl)coformycin aglycone; 3-(2'-(6"-methyl-3"-(tetrazol-5"-yl)phenyl)ethyl) coformycin aglycone; 3-(5'-carboxy-5'-carbobenzyloxypentyl coformycin aglycone; 3-(2'-(3"-carboxynaphthyl)ethyl)coformycin aglycone; 3-[2-(3-carboxy-5,6,7,8-tetrahydro-1-naphthyl)ethyl]coformycin aglycone; and 3-[2-(4-bromo-3-carboxy-5,6,7,8-tetrahydro-1-naphthyl)ethyl]coformycin aglycone.

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis;* J. D. Morrison and J. W. Scott, Eds.; Academic Press Publishers: New York, 1983–1985, Volumes 1–5; *Principles of Asymmetric Synthesis,* R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC;* G. Subramanian, Ed.; VCH Publishers: New York, 1994; *Chiral Separations by HPLC;* A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions,* Volume 37, (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The compounds of the present invention should selectively increase adenosine levels only in tissue undergoing hypoxic or ischaemic stress, as these are the only sites which have significant AMP concentrations due to net ATP breakdown via the ATP-AMP-adenosine pathway. Thus, side effects resulting from adenosine accumulation and receptor activation in non-target tissue should be greatly reduced compared to previously reported examples.

It is believed that compounds of Formula I will be effective in preventing or treating damage to the retina and optic nerve, particularly damage resulting from ischaemic or hypoxic stress, by elevating adenosine levels in the target tissue via selective inhibition of AMPDA. The compounds can be used specifically to treat damage associated with branch and central vein/artery occlusion and anterior ischaemic optic neuropathy. The compounds are also useful for treating damage arising from the presence of cyto or neurotoxic entities, such as glutamate and other excitatory amino acids or peptides, excess intracellular calcium, and free radicals. In particular, the compounds can be useful in treating damage associated with branch and central vein/artery occlusion, trauma, edema, angle-closure glaucoma, open-angle glaucoma, age related macular degeneration (ARMD), retinitis pigmentosa (RP), retinal detachments, damage associated with laser therapy, including photodynamic therapy (PDT), and surgical light induced iatrogenic retinopathy.

Using the above described techniques, other AMPDA inhibitor/s may become known, and are therefore, contemplated by the present invention and within the definition of AMPDA.

The AMPDA inhibitor/s may be contained in various types of pharmaceutical compositions, in accordance with formulation techniques known to those skilled in the art. For example, the compounds may be included in tablets, capsules, solutions, suspensions, and other dosage forms adapted for oral administration; solutions and suspensions adapted for parenteral use; and solutions and suspensions adapted for topical ophthalmic, depot, or intra-ocular injection. Solutions, suspensions, and other dosage forms adapted for depot or intra-ocular injection are particularly preferred for the prevention or treatment of acute or chronic retinal or optic nerve head damage. Compositions can also be delivered according to the teachings in WO 96/05840, which is incorporated herein by reference.

The present invention is particularly directed to the provision of compositions adapted for treatment of retinal and optic nerve head tissues. The ophthalmic compositions of the present invention will include one or more AMPDA inhibitor/s and a pharmaceutically acceptable vehicle. Various types of vehicles may be used. The vehicles will generally be aqueous in nature. Aqueous solutions are generally preferred, based on ease of formulation, as well as a patient's ability to easily administer such compositions by means of instilling one to two drops of the solutions in the affected eyes. However, the AMPDA inhibitor/s of the present invention may also be readily incorporated into other types of compositions, such as suspensions, viscous or semi-viscous gels, or other types of solid or semi-solid compositions. Suspensions may be preferred for AMPDA inhibitor/s which are relatively insoluble in water. The ophthalmic compositions of the present invention may also include various other ingredients, such as buffers, preservatives, co-solvents, and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

When the AMPDA inhibitor/s of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex. USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice,* Ed., G. L. Spaeth. W. B. Sanders Co., Philadelphia, Pa., U.S.A., (1990).

The route of administration (e.g., topical, ocular injection, parenteral, or oral) and the dosage regimen will be determined by skilled clinicians, based on factors such as the exact nature of the condition being treated, the severity of the condition, and the age and general physical condition of the patient.

As indicated above, use of AMPDA inhibitor/s to prevent or reduce damage to retinal and optic nerve head tissues at the cellular level is a particularly important aspect of the present invention. Ophthalmic conditions which may be treated include, but are not limited to, retinopathies, macular degeneration, ocular ischemia, glaucoma, and damage associated with injuries to ophthalmic tissues, such as ischemia reperfusion injuries. photochemical injuries, and injuries associated with ocular surgery, particularly injuries to the retina or optic nerve head by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or non-invasive ophthalmic procedures, or other types of surgery.

In general, the doses used for the above described purposes will vary, but will be in an effective amount to prevent, reduce or ameliorate retinal or optic nerve head tissue damage resulting from any of the above listed conditions. As used herein, the term "pharmaceutically effective amount" refers to an amount of one or more AMPDA inhibitor/s which will prevent, reduce, or ameliorate chronic or acute retinal or optic nerve head damage resulting from ischemic or hypoxic conditions in a human patient. The doses used for any of the above-described purposes will generally be from about 0.01 to about 100 milligrams per kilogram of body weight (mg/kg), administered one to four times per day. When the compositions are dosed topically, they will generally be in a concentration range of from 0.001 to about 5% w/v, with 1–2 drops administered 1–4 times per day.

As used herein, the term "pharmaceutically acceptable carrier" refers to any formulation which is safe, and provides the appropriate delivery for the desired route of administration of an effective amount of at least one compound of the present invention.

The following Examples 1 and 2 are formulations useful for intraocular periocular, or retrobulbar injection or perfusion.

| Component | % w/v |
|---|---|
| AMPDA | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |
| AMPDA | 0.1 |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

EXAMPLE 3

An AMPDA inhibitor/s of the present invention can be formulated in an ocular irrigating solution used during ophthalmic surgery to treat retinal or optic nerve head damage resulting from trauma due to injury or prevent damages resulting from the invasive nature of the surgery. The concentration of the AMPDA inhibitor/s in the irrigating solution will range from 0.001 to 5% w/v The following tablet formulation can be made pursuant to U.S. Pat. No. 5,049,586, incorporated herein by reference.

| Component | % w/v |
|---|---|
| 3-[2-(4-bromo-3-carboxy-5,6,7,8-tetrahydro-1-naphthyl)ethyl]coformycin aglycone | 60 |
| Magnesium oxide | 20 |
| Corn starch | 15 |
| Polyvinylpyrrolidone | 3 |
| Sodium carboxymethylcellulose | 1 |
| Magnesium sterate | 0.8 |

I claim:
1. A method for treating or preventing damage to the eye wherein the damage is associated with a condition selected from the group consisting of branch and central vein/artery occlusion, angle-closure glaucoma, open-angle glaucoma, anterior ischaemic optic neuropathy, ARMD, RP, retinal detachments, laser therapy, and surgical light induced iato- genic retinopathy which comprises administration of a pharmaceutically effective amount of a compound of Formula I:

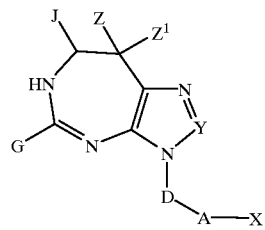

wherein:

Y=—C(K)—;

K=H, halo, azido, or amino;

G=H lower alkyl, amino;

Z=azido, hydroxy, thio, lower acyloxy, or lower thioacyloxy;

Z'=H or lower alkyl;

J=H or lower alkyl;

B=straight or branched divalent group selected from lower alkylene, lower alkylenylaryl, lower alkylenylamino, lower alkylenylaminoalkylene, lower alkylenylaminoaryl, lower alkylenyloxyaryl, lower alkylenylacylamino, lower alkylenyloxyalkyenylaryl, lower alkylenylacylaminoalkylene, lower alkyleneoxy, lower alkoxyalkyl, lower alkylenethio, lower alkylthioalkyl, lower alkynyl, lower alkenyl, alkylcarboxamidoalkyl, alkylcarboxamidoalkylaryl, hydroxylated lower alkylene, halogenated lower alkylene, halogenated lower alkylenylaryl, alkylenetetrazolo, alkylene-3H-1,2,3,5-oxythiodiazolo, alkylenethiazolidine-2,4-diono, alkyleneoxazolidin-2,4-diono or is a direct link;

A=a divalent group selected from a straight or branched alicyclic group, a straight or branched heteroalicyclic group, aryl group or heteroaryl group, all optionally substituted with substituents independently selected from lower alkyl, lower aryl, lower aryloxy, aralkyl, perhaloalkoxy, aralkoxy, heteroaryl, heteroaryloxy, heteroarylalkyl, heteroaralkoxy, azido, amino, guanidino, halogen, hydroxy, lower alkoxy, lower alkylthio, carboxyalkyl, carboxyl carboxamido, carboxamidoalkylaryl, carboxamidoaryl, aminocarboxamidoalkyl, cyano, lower perhaloalkyl, or is a direct link;

X=H, lower alkyl, lower alkoxy, halogen, OH, acyloxy, thio, amino, azido, cyano, carboxyl, carboxyalkyl, carboxyaryl, carboxyaralkyl, tetrazolo, 3H-1,2,3,5-oxythiodiazolo, thiazolidine-2,4-diono, oxazolidin-2,4-diono, carboxamido, carboxamidoalkyl, carboxamidoaralkyl, carboxamidoaryl, guanidino, -PO3EE', or C(W)CO2 E(COQ);

E and E'=same or different=H, lower alkyl, aryl or aralkyl;

W=H, lower alkyl, lower alkoxy, aralkoxy, lower alkylthio, alkylamino, OH, amino, arylamino, aralkylamino or aryloxy;

Q=lower alkyl, lower alkoxy, aralkoxy, lower alkylthio, alkylamino, OH, amino, arylamino, aralkylamino or aryloxy;

and pharmaceutically acceptable salts and prodrugs thereof, in a pharmaceutically acceptable carrier.

2. The method of claim 1 wherein the compound is selected from the group consisting of (1'S,2'S,5'S)-3-(6',6'-dimethyl[3.1.1]-bicyclohept-2'-methyl)coformycin aglycone; 3-(5'-carboxy-6'-phenylhexyl)coformycin aglycone; 3-(5'-carbox-N-benzylamido-5'-carboxyhexyl)coformycin aglycone; 3-(2'-(3"-carboxy-6"-methylphenyl)ethyl)coformycin aglycone; 3-(2'-(6"-methyl-3"-(tetrazol-5'"-yl)phenyl)ethyl)coformycin aglycone; 3-(5'-carboxy-5'-carbobenzyloxypentyl coformycin aglycone; 3-(2'-(3"-carboxynaphthyl)ethyl)coformycin aglycone; 3-[2-(3-carboxy-5,6,7,8-tetrahydro-1-naphthyl)ethyl]coformycin aglycone; and 3-[2-(4-bromo-3-carboxy-5,6,7,8-tetrahydro-1-naphthyl)ethyl]coformycin aglycone.

* * * * *